United States Patent [19]

Mori et al.

[11] Patent Number: 5,446,129

[45] Date of Patent: Aug. 29, 1995

[54] PEPTIDE OR ITS SALT FOR AUTOIMMUNE HYPERTHYROIDISM CONTAINING IT

[75] Inventors: Toru Mori; Hideo Sugawa, both of Kyoto; Nobutoshi Yamada; Yoshimichi Ueda, both of Kusatsu, all of Japan

[73] Assignee: Ishihara Sangyo Kaisha Ltd., Osaka, Japan

[21] Appl. No.: 285,777

[22] Filed: Aug. 4, 1994

Related U.S. Application Data

[63] Continuation of Ser. No. 780,463, Oct. 22, 1991, abandoned.

[30] Foreign Application Priority Data

Oct. 24, 1990 [JP] Japan .................................. 2-286802
Nov. 1, 1990 [JP] Japan .................................. 2-296886

[51] Int. Cl.⁶ ..................... A61K 38/00; C07K 5/00; C07K 7/00; C07K 14/00
[52] U.S. Cl. ................................................... 530/324
[58] Field of Search ........................... 530/324; 514/12

[56] References Cited

FOREIGN PATENT DOCUMENTS

WO9109121 6/1991 WIPO .

OTHER PUBLICATIONS

Russo et al., Chemcial Abstracts, vol. 116., p. 79, Abs No. 15935w.
Nagayama et al., Bioch., Biophys. Res. Comm., vol. 165, No. 3, pp. 1184–1190, 1989.
Morris II, et al., J. Clin Endocr. Metab., vol. 67 No. 4, pp. 707–712, 1988.
Biochemical And Biophysical Research Communications, vol. 178, No. 1, Jul. 15, 1991, pp. 165–172, T. Mori et al., "A Synthetic Oligopeptide Derived From Human Thyrotropin Receptor Sequence Binds To Graves' Immunoglobulin And Inhibits Thyroid Stimulating Antibody Activity But Lacks Interactions With TSH".
Biochemical And Biophysical Research Communications, vol. 165, No. 3, Dec. 29, 1989, pp. 1250–1255, F. Libert, et al., "Cloning, Sequencing And Expression Of The Human Thyroptropin (TSH) Receptor. Evidence For Binding Of Antibodies".

*Primary Examiner*—Jill Warden
*Assistant Examiner*—A. M. Davenport
*Attorney, Agent, or Firm*—Oblon, Spivak, McClelland, Maier, & Neustadt

[57] ABSTRACT

A peptide having the formula:

A—B—C wherein A is a hydrogen atom, Glu, Phe Glu—, Phe Phe Glu— or an amino acid sequence as shown by SEQ ID NO:1 in the Sequence Listing, B is an amino acid sequence as shown by SEQ ID NO:2, and C is a hydroxyl group, Glu, —Glu Ile, —Glu Ile Ile or an amino acid sequence as shown by SEQ ID NO:3, 4, 5, 6, 7, 8, 9, 10, 11, 12, 13, 14, 15 or 16, and containing from 6 to 25 amino acids; or its salt.

5 Claims, 1 Drawing Sheet

SEQUENCE LISTING ( 1 ) GENERAL INFORMATION:

( i i i ) NUMBER OF SEQUENCES: 39

( 2 ) INFORMATION FOR SEQ ID NO:1:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:1:

Val Phe Phe Gly
1

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

Glu Gln Glu Asp
1

( 2 ) INFORMATION FOR SEQ ID NO:3:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

Glu Ile Ile Gly
1

( 2 ) INFORMATION FOR SEQ ID NO:4:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

Glu Ile Ile Gly Phe
1                 5

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

Glu Ile Ile Gly Phe Gly
1                 5

( 2 ) INFORMATION FOR SEQ ID NO:6:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

Glu Ile Ile Gly Phe Gly Gln
1                 5

( 2 ) INFORMATION FOR SEQ ID NO:7:

( i ) SEQUENCE CHARACTERISTICS:
  ( A ) LENGTH: 8 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:7:

```
Glu  Ile  Ile  Gly  Phe  Gly  Gln  Glu
1                  5
```

( 2 ) INFORMATION FOR SEQ ID NO:8:

( i ) SEQUENCE CHARACTERISTICS:
  ( A ) LENGTH: 9 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:8:

```
Glu  Ile  Ile  Gly  Phe  Gly  Gln  Glu  Leu
1                  5
```

( 2 ) INFORMATION FOR SEQ ID NO:9:

( i ) SEQUENCE CHARACTERISTICS:
  ( A ) LENGTH: 10 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:9:

```
Glu  Ile  Ile  Gly  Phe  Gly  Gln  Glu  Leu  Lys
1                  5                        10
```

( 2 ) INFORMATION FOR SEQ ID NO:10:

( i ) SEQUENCE CHARACTERISTICS:
  ( A ) LENGTH: 11 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:10:

```
Glu  Ile  Ile  Gly  Phe  Gly  Gln  Glu  Leu  Lys  Asn
1                  5                        10
```

( 2 ) INFORMATION FOR SEQ ID NO:11:

( i ) SEQUENCE CHARACTERISTICS:
  ( A ) LENGTH: 12 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:11:

```
Glu  Ile  Ile  Gly  Phe  Gly  Gln  Glu  Leu  Lys  Asn  Pro
1                  5                        10
```

( 2 ) INFORMATION FOR SEQ ID NO:12:

( i ) SEQUENCE CHARACTERISTICS:
  ( A ) LENGTH: 13 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:12:

```
Glu  Ile  Ile  Gly  Phe  Gly  Gln  Glu  Leu  Lys  Asn  Pro  Gln
1                  5                        10
```

( 2 ) INFORMATION FOR SEQ ID NO:13:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:13:

```
Glu  Ile  Ile  Gly  Phe  Gly  Gln  Glu  Leu  Lys  Asn  Pro  Gln  Glu
1                  5                        10
```

( 2 ) INFORMATION FOR SEQ ID NO:14:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:14:

```
Glu  Ile  Ile  Gly  Phe  Gly  Gln  Glu  Leu  Lys  Asn  Pro  Gln  Glu  Glu
1                  5                        10                       15
```

( 2 ) INFORMATION FOR SEQ ID NO:15:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:15:

```
Glu  Ile  Ile  Gly  Phe  Gly  Gln  Glu  Leu  Lys  Asn  Pro  Gln  Glu  Glu  Thr
1                  5                        10                       15
```

( 2 ) INFORMATION FOR SEQ ID NO:16:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:16:

```
Glu  Ile  Ile  Gly  Phe  Gly  Gln  Glu  Leu  Lys  Asn  Pro  Gln  Glu  Glu  Thr
1                  5                        10                       15
Leu
```

( 2 ) INFORMATION FOR SEQ ID NO:17:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:17:

```
Val  Phe  Phe  Glu  Glu  Gln  Glu  Asp  Glu  Ile  Ile  Gly  Phe  Gly  Gln  Glu
```

```
            1                  5                      10                      15
```

Leu Lys Asn Pro Gln Glu Glu Thr Leu
                20                      25

(2) INFORMATION FOR SEQ ID NO:18:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:18:

Phe Glu Glu Gln Glu Asp
1                   5

(2) INFORMATION FOR SEQ ID NO:19:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:19:

Glu Glu Gln Glu Asp Glu
1                   5

(2) INFORMATION FOR SEQ ID NO:20:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:20:

Glu Gln Glu Asp Glu Ile
1                   5

(2) INFORMATION FOR SEQ ID NO:21:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:21:

Phe Phe Glu Glu Gln Glu Asp
1                   5

(2) INFORMATION FOR SEQ ID NO:22:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:22:

Glu Gln Glu Asp Glu Ile Ile
1                   5

(2) INFORMATION FOR SEQ ID NO:23:

(i) SEQUENCE CHARACTERISTICS:
   (A) LENGTH: 8 amino acids
   (B) TYPE: amino acid
   (D) TOPOLOGY: linear (ii) MOLECULE TYPE: peptide (xi) SEQUENCE DESCRIPTION: SEQ ID NO:23:

Phe Phe Glu Glu Gln Glu Asp Glu
1               5

(2) INFORMATION FOR SEQ ID NO:24:

(i) SEQUENCE CHARACTERISTICS:
      (A) LENGTH: 8 amino acids
      (B) TYPE: amino acid
      (D) TOPOLOGY: linear (ii) MOLECULE TYPE: peptide (xi) SEQUENCE DESCRIPTION: SEQ ID NO:24:

Phe Glu Glu Gln Glu Asp Glu Ile
1               5

(2) INFORMATION FOR SEQ ID NO:25:

(i) SEQUENCE CHARACTERISTICS:
      (A) LENGTH: 8 amino acids
      (B) TYPE: amino acid
      (D) TOPOLOGY: linear (ii) MOLECULE TYPE: peptide (xi) SEQUENCE DESCRIPTION: SEQ ID NO:25:

Glu Glu Gln Glu Asp Glu Ile Ile
1               5

(2) INFORMATION FOR SEQ ID NO:26:

(i) SEQUENCE CHARACTERISTICS:
      (A) LENGTH: 8 amino acids
      (B) TYPE: amino acid
      (D) TOPOLOGY: linear (ii) MOLECULE TYPE: peptide (xi) SEQUENCE DESCRIPTION: SEQ ID NO:26:

Val Phe Phe Glu Glu Gln Glu Asp
1               5

(2) INFORMATION FOR SEQ ID NO:27:

(i) SEQUENCE CHARACTERISTICS:
      (A) LENGTH: 9 amino acids
      (B) TYPE: amino acid
      (D) TOPOLOGY: linear (ii) MOLECULE TYPE: peptide (xi) SEQUENCE DESCRIPTION: SEQ ID NO:27:

Val Phe Phe Glu Glu Gln Glu Asp Glu
1               5

(2) INFORMATION FOR SEQ ID NO:28:

(i) SEQUENCE CHARACTERISTICS:
      (A) LENGTH: 9 amino acids
      (B) TYPE: amino acid
      (D) TOPOLOGY: linear (ii) MOLECULE TYPE: peptide ( x i ) SEQUENCE DESCRIPTION: SEQ ID NO:28:

Phe Glu Glu Gln Glu Asp Glu Ile Ile
1               5

( 2 ) INFORMATION FOR SEQ ID NO:29:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:29:

Glu Glu Gln Glu Asp Glu Ile Ile Gly
1               5

( 2 ) INFORMATION FOR SEQ ID NO:30:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:30:

Val Phe Phe Glu Glu Gln Glu Asp Glu Ile
1               5                   10

( 2 ) INFORMATION FOR SEQ ID NO:31:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:31:

Phe Glu Glu Gln Glu Asp Glu Ile Ile Gly
1               5                   10

( 2 ) INFORMATION FOR SEQ ID NO:32:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:32:

Glu Gln Glu Asp Glu Ile Ile Gly Phe Gly
1               5                   10

( 2 ) INFORMATION FOR SEQ ID NO:33:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:33:

Phe Glu Glu Gln Glu Asp Glu Ile Ile Gly Phe Gly
1               5                   10

( 2 ) INFORMATION FOR SEQ ID NO:34:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:34:

```
Val  Phe  Phe  Glu  Glu  Gln  Glu  Asp  Glu  Ile  Ile  Gly  Phe  Gly
 1                  5                            10
```

( 2 ) INFORMATION FOR SEQ ID NO:35:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:35:

```
Phe  Glu  Glu  Gln  Glu  Asp  Glu  Ile  Ile  Gly  Phe  Gly  Gln  Glu  Leu
 1                  5                            10                      15
```

( 2 ) INFORMATION FOR SEQ ID NO:36:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:36:

```
Val  Phe  Phe  Glu  Glu  Gln  Glu  Asp  Glu  Ile  Ile  Gly  Phe  Gly  Gln  Glu
 1                  5                            10                      15
Leu
```

( 2 ) INFORMATION FOR SEQ ID NO:37:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:37:

```
Val  Phe  Phe  Glu  Glu  Gln  Glu  Asp  Glu  Ile  Ile  Gly  Phe  Gly  Gln  Glu
 1                  5                            10                      15
Leu  Lys  Asn  Pro
               20
```

( 2 ) INFORMATION FOR SEQ ID NO:38:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:38:

```
Phe  Glu  Glu  Gln  Glu  Asp  Glu  Ile  Ile  Gly  Phe  Gly  Gln  Glu  Leu  Lys
 1                  5                            10                      15
Asn  Pro  Gln  Glu
          20
```

(2) INFORMATION FOR SEQ ID NO:39:

(i) SEQUENCE CHARACTERISTICS:
(A) LENGTH: 23 amino acids
(B) TYPE: amino acid
(D) TOPOLOGY: linear (ii) MOLECULE TYPE: peptide (xi) SEQUENCE DESCRIPTION: SEQ ID NO:39:

```
Phe Glu Glu Gln Glu Asp Glu Ile Ile Gly Phe Gly Gln Glu Leu Lys
1               5                   10                  15
Asn Pro Gln Glu Glu Thr Leu
            20
```

PEPTIDE OR ITS SALT FOR AUTOIMMUNE HYPERTHYROIDISM CONTAINING IT

This application is a Continuation of application Ser. No. 07/780,463, filed on Oct. 22, 1991, now abandoned.

The present invention relates to a novel peptide or its salt and a diagnostic or therapeutic agent for autoimmune hyperthyroidism, which contains, as active ingredient, a peptide or its salt useful against thyroid stimulating antibody (TSAb), i.e. one of thyroid stimulating hormone (TSH) receptor autoantibodies, which is considered to be one of important causes for autoimmune hyperthyroidism.

The above-mentioned TSAb which is considered to be one of causes for autoimmune hyperthyroidism, relates directly to pathogenesis. Its quantitative change is considered to be an important marker for activity of the disease. Heretofore, for the measurement of the above-mentioned autoantibodies, a stimulation assay method wherein production of cyclic adenosin 3′,5′-monophosphate (cAMP) by the activation of adenylate cyclase, is used as an index, and a binding inhibition assay method which is a radioimmunoassay using $^{125}$I-TSH (thyroid stimulating hormone), have been widely employed. As the stimulation assay method, a method by S. Kosugi et al. (Endocrinology, Vol. 125, No. 1, p 410 (1989)) is known. According to this method, rat established thyroid cell line FRTL5 is employed to measure the produced cAMP by the activation of adenylate cyclase which in turn is induced by the binding of TSAb with TSH receptor. The activity of TSAb is determined by the measured amount as an index. On the other hand, B. R. Smith et al. have established a standard binding assay method (Clinical Endocrinology, Vol. 17, p 409 (1982)). This method utilizes $^{125}$I-TSH and its principle is the quantification of inhibition by TSH receptor autoantibodies against the binding of $^{125}$I-TSH with solubilized TSH receptor from porcine thyroid. The TSH receptor autoantibodies include TSAb and TBII (TSH-binding inhibitory immunogloblin), but the results of these methods do not tell which one or both are bound with the TSH receptor.

The conventional methods involve cumbersome operations in the measurement, and it is desired to develop a simpler method.

The present inventors have found that a certain specific peptide specifically recognize TSAb and has an activity of inhibiting the binding of TSAb and TSH receptor and that such peptide is potently useful as a diagnostic or therapeutic agent for autoimmune hyperthyroidism. The present invention has been accomplished on the basis of this discovery.

The present invention relates to a synthetic peptide having a sequence corresponding to a part of the structure of human TSH receptor.

The present invention provides a peptide having the formula:

A—B—C wherein A is a hydrogen atom, Glu, Phe Glu—, Phe Phe Glu— or an amino acid sequence as shown by SEQ ID NO:1 in the Sequence Listing, B is an amino acid sequence as shown by SEQ ID NO:2, and C is a hydroxyl group, Glu, —Glu Ile, —Glu Ile Ile or an amino acid sequence as shown by SEQ ID NO:3, 4, 5, 6, 7, 8, 9, 10, 11, 12, 13, 14, 15 or 16, and containing from 6 to 25 amino acids; or its salt (hereinafter referred to simply as a peptide), and a diagnostic or therapeutic agent for autoimmune hyperthyroidism containing it.

Here, the salt of the peptide may be any salt so long as it is pharmaceutically acceptable. For example, an alkali metal salt such as a sodium or potassium salt, an alkaline earth metal salt such as a magnesium or calcium salt, an amine salt such as a monomethylamine or triethylamine salt, or a quaternary ammonium salt such as a trimethylethylammonium or tetramethylammonium salt, may be mentioned.

The above peptide of the present invention may be explained in accordance with SEQ ID NO:17 in the Sequential Listing as follows. Namely, the partial sequence of from the 5th Glu to the 8th Asp in SEQ ID NO:17 is connected with $^4$Glu as a constituting amino acid or with $^3$Phe—$^4$Glu—, $^2$Phe—$^4$Glu— or $^1$Val—$^4$Glu— as a constituting amino acid partial sequence towards N-terminal direction from the $^5$Glu, or connected with $^9$Glu as a constituting amino acid, or with —$^9$Glu—$^{10}$Ile, —$^9$Glu—$^{11}$Ile, —$^9$Glu—$^{12}$Gly, —$^9$Glu—$^{13}$Phe, —$^9$Glu—$^{14}$Gly, —$^9$Glu—$^{15}$Gln, —$^9$Glu—$^{16}$Glu, —$^9$Glu—$^{17}$Leu, —$^9$Glu—$^{18}$Lys, —$^9$Glu—$^{19}$Asn, —$^9$Glu—$^{20}$Pro, —$^9$Glu—$^{21}$Gln, —$^9$Glu—$^{22}$Glu, —$^9$Glu—$^{23}$Glu, —$^9$Glu—$^{24}$Thr or —$^9$Glu—$^{25}$Leu as a constituting amino acid partial sequence towards the C-terminal direction from the 8th Asp. Such partial sequence is connected in either the N-terminal direction or the C-terminal direction or in both directions. When the above partial sequence is not connected in the N-terminal direction or in the C-terminal direction, a hydrogen atom is bonded to the 5th Glu, or a hydroxyl group is bonded to the 8th Asp. Further, the above peptide is constituted by from 6 to 25 amino acids.

The specific peptide of the present invention may, for example, be a peptide having an amino acid sequence represented by:

(1) from the 3rd Phe to the 8th Asp (SEQ ID NO:18),
(2) from the 4th Glu to the 9th Glu (SEQ ID NO:19),
(3) from the 5th Glu to the 10th Ile (SEQ NO: 20),
(4) from the 2nd Phe to the 8th Asp (SEQ NO: 21),
(5) from the 5th Glu to the 11th Ile (SEQ NO: 22),
(6) from the 2nd Phe to the 9th Glu (SEQ NO: 23),
(7) from the 3rd Phe to the 10th Ile (SEQ NO: 24),
(8) from the 4th Glu to the 11th Ile (SEQ NO: 25),
(9) from the 1st Val to the 8th Asp (SEQ NO: 26),
(10) from the 1st Val to the 9th Glu (SEQ NO: 27),
(11) from the 3rd Phe to the 11th Ile (SEQ NO: 28),
(12) from the 4th Glu to the 12th Gly (SEQ NO: 29),
(13) from the 1st Val to the 10th Ile (SEQ NO: 30),
(14) from the 3rd Phe to the 12th Gly (SEQ NO: 31),
(15) from the 5th Glu to the 14th Gly (SEQ NO: 32),
(16) from the 3rd Phe to the 14th Gly (SEQ NO: 33),
(17) from the 1st Val to the 14th Gly (SEQ NO: 34),
(18) from the 3rd Phe to the 17th Leu (SEQ NO: 35),
(19) from the 1st Val to the 17th Leu (SEQ NO: 36),
(20) from the 1st Val to the 20th Pro (SEQ NO: 37),
(21) from the 3rd Phe to the 22nd Glu (SEQ NO: 38),
(22) from the 3rd Phe to the 25th Leu (SEQ NO: 39), or
(23) from the 1st Val to the 25th Leu (SEQ NO: 40) in the amino acid sequence as shown in SEQ ID NO:17 in the Sequence Listing; or its salt.

Among them, preferred is a peptide having an amino acid sequence represented by:
(1) from the 1st Val to the 10th Ile (SEQ NO: 30),
(2) from the 1st Val to the 14th Gly (SEQ NO: 34), (3) from the 3rd Phe to the 17th Leu (SEQ NO: 35),
(4) from the 1st Val to the 20th Pro (SEQ NO: 37),
(5) from the 1st Val to the 25th Leu (SEQ NO: 40),
(6) from the 3rd Phe to the 14th Gly (SEQ NO: 33),
(7) from the 1st Val to the 8th Asp (SEQ NO: 26), or
(8) from the 5th Glu to the 14th Gly (SEQ NO: 32) in the amino acid sequence as shown in SEQ ID NO:17 in the Sequence Listing; or its salt.

More preferred is a peptide having an amino acid sequence represented by:
(1) from the 1st Val to the 10th Ile (SEQ NO: 30),
(2) from the 1st Val to the 14th Gly (SEQ NO: 34),
(3) from the 1st Val to the 25th Leu (SEQ NO: 40),
(4) from the 1st Val to the 8th Asp (SEQ NO: 26), or
(5) from the 5th Glu to the 14th Gly (SEQ NO: 32) in the amino acid sequence as shown in SEQ ID NO:17 in the Sequence Listing; or its salt.

Most preferred is a peptide having an amino acid sequence represented by from the 1st Val to the 14th Gly in the amino acid sequence as shown in SEQ ID NO:17 in the Sequence Listing; or its salt.

BRIEF DESCRIPTION OF THE DRAWING

In the accompanying drawing.

Figure 1:
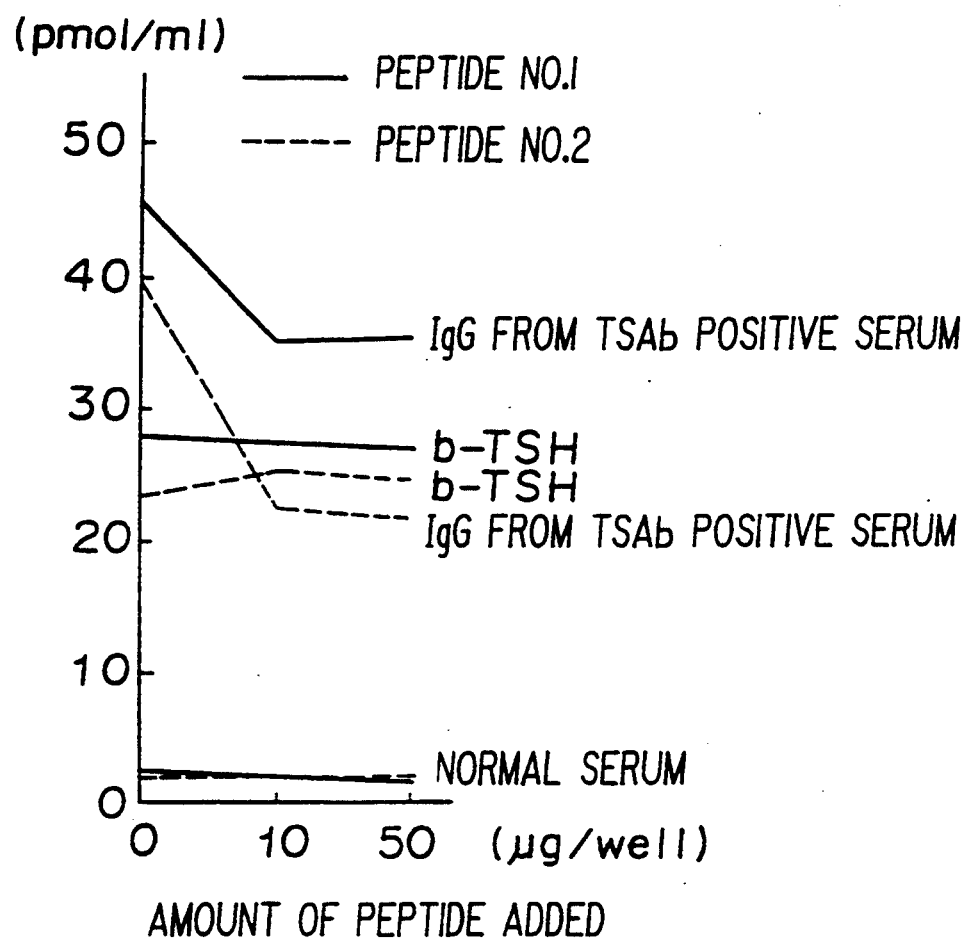
FIG. 1 is a graph showing the influences of the peptides of the present invention over the production of cAMP under stimulation by TSAb or b-TSH in a test wherein rat's thyroid cells were used.

Throughout the present specification, the following abbreviations have the following meanings.
Lys: L-lysine,
Glu: L-glutamic acid
Pro: L-proline
Phe: L-phenylalanine
Gln: L-glutamine
Asp: L-aspartic acid
Thr: L-threonine
Asn: L-asparagine
Val: L-valine
Ile: L-isoleucine
Leu: L-leucine
Gly: glycine
PAM: 4-oxymethylphenylacetamidemethyl
Boc: t-butoxycarbonyl
Fmoc: 9-fluorenylmethyloxycarbonyl
TFA: trifluoroacetic acid
TFMSA: trifluoromethanesulfonic acid The peptide of the present invention can be obtained by a conventional method such as a liquid phase method or a solid phase method. More simply, it can be obtained by means of a commercially available peptide synthesizer by a solid phase method.

In the solid phase method, an amino acid corresponding to the amino acid residue at the C-terminal side of the peptide which is supported on a polymer support, is coupled to the C-terminal side of the peptide to form a peptide bond. For this coupling, a conventional method such as a DCC method, an acetic anhydride method or an activated esterification method can, for example, be employed. As a protecting group for an α-amino group, a Boc group or a Fmoc group may be employed. For example, when the synthesis is conducted by means of a peptide autosynthesizer, it is preferred to select the amino acid properly taking into consideration the nature of the protecting group in accordance with the instructions given in the manual for the synthesizer.

As protecting groups for protected amino acids to be used in the solid phase method, those which are commonly employed in the peptide synthesis can be employed. For example, when a Boc group is used for an α-amino group, a benzyl group or a cyclohexyl group to be protected by an ester group, may be employed for a carboxyl group of Asp or Glu; a benzyl group may be employed for a hydroxyl group of Thr; and a p-chlorobenzyloxycarbonyl group may be employed for a side chain amino group of Lys.

When the synthesis is conducted by the liquid phase method, it can be conducted in accordance with a conventional peptide synthesis, like in the case of the solid phase method. As a known method, there may be mentioned, for example, a method disclosed in "Fundamentals and Experiments for Peptide Synthesis" edited by Nobuo Izumiya et al, published by Maruzen K.K., (1975).

Then, when a Boc group is employed as a protecting group for an α-amino group, cleavage from the support and removal of the protective group, can be conducted by means of e.g. TFMSA or hydrogen fluoride containing a scavenger. As the scavenger, thioanisole, ethanedithiol, dimethylsulfide, or the like, may be employed. Further, when a Fmoc group is employed as a protective group for an α-amino group, a mixture comprising phenol and TFA, may, for example, be employed.

For purification of the peptide, an ion exchange resin, partition chromatography, gel chromatography and reverse phase liquid chromatography which are commonly employed, can be used alone or in combination. The amino acid composition of the purified peptide can readily be measured by an amino acid analyzer.

The peptide of the present invention is useful as a means to simply and conveniently grasp the quantitative change of TSAb and thus is potently useful as a diagnostic agent for autoimmune hyperthyroidism, and it also has an activity to inhibit the binding of TSAb and TSH receptor and thus is useful as a therapeutic agent for autoimmune hyperthyroidism.

By a test in which the peptide of the present invention is used, the presence of TSAb (thyroid stimulating antibody) can be detected, and autoimmune hyperthyroidism can be treated by administering a therapeutically effective amount of the peptide to a patient. To be used as a diagnostic or therapeutic agent, the peptide of the present invention may be formulated into a diagnostic or therapeutic composition, which contains an effective amount thereof together with a diagnostically or pharmaceutically acceptable carrier.

When the peptide of the present invention is used as a diagnostic agent, TSAb can be quantitatively analyzed by using the peptide labeled with a radioisotope or enzyme, utilizing the characteristic such that the peptide specifically binds TSAb in the patient serum. Otherwise, the above peptide may be supported on a suitable carrier and administered to an animal such as a mouse, rat or rabbit for immunization, and the antibody thereby obtained may be utilized for a quantitative analysis of TSAb.

When the peptide of the present invention is used as a therapeutic agent, it may be formulated into an oral drug such as tablets, capsules, granules or powder, or may be formulated into a non-oral drug such as an injection solution. The dose of the drug varies in accordance to the symptoms, the age and the weight of the patient, the manner of administration, etc. and must be determined by a suitable test by a medical doctor.

Now, the present invention will be described in further detail with reference to Examples. However, it should be understood that the present invention is by no means restricted by such specific Examples.

EXAMPLE 1

Peptide No. 1 peptide having an amino acid sequence represented by from the 1st Val to the 10th Ile of SEQ ID NO:17 in the Sequence Listing)

Using 658 mg (Ile content: 0.76 mmol/g) of Boc—Ile—PAM resin (set in a peptide autosynthesizer as described hereinafter) as a starting material, the desired peptide No. 1 was synthesized by a solid phase method by means of a peptide autosynthesizer (430A Model, manufactured by Applied Biosystems Corporation).

Namely, in accordance with a conventional method, 2 mmol of each of 10 L-form amino acids was sequentially reacted from the C-terminal (carboxyl terminus) Ile according to the above-mentioned amino acid sequence to obtain 1.4 g of a protected peptide on resin.

With respect to protection of side chain functional groups of the amino acids used in this reaction, the carboxyl group of Asp or Glu was protected by a benzyl group.

After drying, 1 g of this protected peptide on resin was stirred in a liquid mixture comprising 0.5 ml of ethanedithiol and 1 ml of thioanisole for 10 minutes under cooling with ice. Then, 10 ml of TFA was added thereto, and the mixture was stirred for 10 minutes. To this mixture, 1 ml of TFMSA was added, and the mixture was stirred for 10 minutes and then further stirred at room temperature for 50 minutes.

Then, 50 ml of dry ethyl ether was added to precipitate a crude peptide. By a glass filter, the crude peptide and the cleaved resin were subjected to filtration. To the crude peptide on the glass filter, 5 ml of TFA was added and the crude peptide was dissolved to obtain a TFA solution. To this solution, dry ethyl ether was added to obtain a precipitate of the crude peptide. The precipitate was separated and then washed with dry ethyl ether a few times and then dried under reduced pressure. Then, the precipitate was dissolved in a 500 mM ammonium acetate buffer (pH9.5), followed by freeze drying. 126 mg of a peptide thus obtained was purified by high performance liquid chromatography (HPLC) under the following conditions. Using a column of reverse phase Asahi Pack ODP-90 (manufactured by Asahi Kasei Corporation), separation and purification were conducted with a linear concentration gradient of a 20 mM ammonium acetate buffer (A) (pH8.5) and acetonitrile (B) (in 60 minutes, (B) became 100%, flow rate: 10 ml/min). The necessary elution fraction was concentrated and freeze-dried to obtain 50 mg of the desired peptide.

Peptide No. 1 thus synthesized was subjected to amino acid analysis. The amino acid analysis was conducted by hydrolyzing the peptide with 6N hydrochloric acid at 110° C. for 20 hours and then measuring amino acids by an amino acid analyzer L8,500 (manufactured by Hitachi Seisakusho Corporation).

| Results of the amino acid analysis | | | | | |
| --- | --- | --- | --- | --- | --- |
| | Asp/Asn | Glu/Gln | Val | Ile | Phe |
| Measured value: | 1.05 | 5.01 | 0.96 | 1.03 | 1.95 |
| Theoretical value: | 1 | 5 | 1 | 1 | 2 |

From the results of the above amino acid analysis, it was confirmed that peptide No. 1 i.e. the desired product of the present invention was obtained.

EXAMPLES 2 TO 8

In the same manner as in Example 1, peptides No. 2, No. 3, No. 4, No. 5, No.6, No. 7 and No. 8 were prepared. With respect to protection of side chain functional groups of the amino acids used for the reaction, the carboxyl group of Asp or Glu was protected by a benzyl group, the amino group of Lys was protected by a p-chlorobenzyloxycarbonyl group, and the hydroxyl group of Thr was protected by a benzyl group.

| Peptide No. 2 (peptide having an amino acid sequence represented by from the 1st Val to the 14th Glu of SEQ ID NO: 17) | | | | | | |
| --- | --- | --- | --- | --- | --- | --- |
| | Asp/Asn | Glu/Gln | Gly | Val | Ile | Phe |
| Measured value: | 1.02 | 5.06 | 1.98 | 0.97 | 2.05 | 2.95 |
| Theoretical value: | 1 | 5 | 2 | 1 | 2 | 3 |

| Peptide No. 3 (peptide having an amino acid sequence represented by from the 3rd Phe to the 17th Leu of SEQ ID NO: 17) | | | | | | |
| --- | --- | --- | --- | --- | --- | --- |
| | Asp/Asn | Glu/Gln | Gly | Ile | Leu | Phe |
| Measured value: | 1.00 | 6.96 | 1.97 | 1.90 | 1.04 | 1.93 |
| Theoretical value: | 1 | 7 | 2 | 2 | 1 | 2 |

| Peptide No. 4 (peptide having an amino acid sequence represented by from the 1st Val to the 20th Pro of SEQ ID NO: 17) | | | | | |
| --- | --- | --- | --- | --- | --- |
| | Asp/Asn | Glu/Gln | Pro | Gly | Val |
| Measured value: | 2.11 | 7.45 | 1.05 | 2.09 | 0.74 |
| Theoretical value: | 2 | 7 | 1 | 2 | 1 |

| | Ile | Leu | Phe | Lys |
| --- | --- | --- | --- | --- |
| Measured value: | 1.90 | 1.03 | 2.88 | 1.00 |
| Theoretical value: | 2 | 1 | 3 | 1 |

| Peptide No. 5 (peptide having an amino acid sequence represented by from the 1st Val to the 25th Leu of SEQ ID NO: 17) | | | | | |
| --- | --- | --- | --- | --- | --- |
| | Asp/Asn | Thr | Glu/Gln | pro | Gly |
| Measured value: | 1.95 | 0.97 | 10.16 | 1.02 | 2.04 |
| Theoretical value: | 2 | 1 | 10 | 1 | 2 |

| | Val | Ile | Leu | Phe | Lys |
| --- | --- | --- | --- | --- | --- |
| Measured value: | 0.94 | 1.95 | 2.02 | 2.96 | 1.02 |
| Theoretical value: | 1 | 2 | 2 | 3 | 1 |

| Peptide No. 6 (peptide having an amino acid sequence represented by from the 3rd Phe to the 14th Gly of SEQ ID NO: 17) | | | | | |
| --- | --- | --- | --- | --- | --- |
| | Asp/Asn | Glu/Gln | Gly | Ile | Phe |
| Measured value: | 1.1 | 5.2 | 1.95 | 1.9 | 2.1 |

-continued

| Theoretical value: | 1 | 5 | 2 | 2 | 2 |

Peptide No. 7
(peptide having an amino acid sequence represented by from the 1st Val to the 8th Asp of SEQ ID NO: 17)

|  | Asp/Asn | Glu/Gln | Val | Phe |
| --- | --- | --- | --- | --- |
| Measured value: | 0.97 | 4.13 | 0.95 | 1.89 |
| Theoretical value: | 1 | 4 | 1 | 2 |

Peptide No. 8
(peptide having an amino acid sequence represented by from the 5th Glu to the 14th Gly of SEQ ID NO: 17)

|  | Asp/Asn | Glu/Gln | Gly | Ile | Phe |
| --- | --- | --- | --- | --- | --- |
| Measured value: | 1.04 | 4.05 | 1.98 | 1.98 | 1.08 |
| Theoretical value: | 1 | 4 | 2 | 2 | 1 |

From the results of the above amino acid analyses, it was confirmed that peptides No. 2 to No. 8 i.e. the desired products of the present invention were obtained.

Using rat established thyroid cell line FRTL5, the influence of the peptide over the production of cAMP under stimulation by TSAb, was examined in accordance with the method of S. Kosugi et al. (Endocrinology, Vol. 125, No. 1, p 410 (1989)). The method will be described as follows.

TEST EXAMPLE 1

Preincubated FRTL5 cells ($1 \times 10^5$ cells/ml) were transferred to a multiplate having 24 wells in an amount of 500 µl per well and incubated in a $CO_2$ incubator for 6 days while changing the medium in the absence of TSH. Then, the medium was removed, and the cells were rinsed and subjected to the test.

180 µl of a solution of IgG from TSAb positive serum from patient with autoimmune thyroid disease or 180 µl of a solution containing 10 µU of b-TSH and 20 µl of a solution containing 0, 10 or 50 µg of the desired peptide were reacted in a test tube at 4° C. for two hours. To this reaction solution, 20 µl of a 0.5 mM solution of 3-isobutyl-1-methylxanthine was added, and 200 µl of this reaction solution was added to the previously prepared FRTL5 cells, followed by incubation at 37° C. for 3 hours.

On the other hand, as control, a test was conducted in the same manner using a normal serum.

With respect to each sample, the amount of cAMP produced under stimulation by TSAb was measured by means of a commercially available cAMP-radioimmunoassay kit (YSI-7701, manufactured by Yamasa-syoyu Corporation). The results are shown in FIG. 1.

As is evident from the results in FIG. 1, peptide No. 1 or peptide No. 2 suppresses the production of cAMP by TSAb by about 25% or by about 50% as compared with the production of cAMP in the absence of the peptide No. 1 or No. 2, respectively, at a concentration of 10 µg/well.

On the other hand, with respect to the influence over b-TSH, both peptides exhibited no substantial activities against the stimulating activity and the binding of b-TSH and TSH receptor.

Thus, it is understood that the peptides of the present invention have activities to inhibit the binding of TSAb and TSH receptor and show no activities to the binding of b-TSH and TSH receptor, and they are able to specifically recognize TSAb.

TEST EXAMPLE 2

Preincubated FRTL5 cells ($1.5 \times 10^5$ cells/ml) were transferred to a multiplate having 96 wells in an amount of 100 µl per well and incubated in a $CO_2$ incubator for 6 days while changing the medium (having TSH excluded). Then, the medium was removed and the cells were rinsed and subjected to the test. 40 µl of a solution of IgG from TSAb positive serum and 10 µl of a solution containing 0, 15 or 30 µg of the desired peptide were reacted in a test tube at 4° C. for 20 hours. To this reaction solution, 5 µl of a 0.5 mM solution of 3-isobutyl-1-methylxanthine was added, and 50 µl of this reaction solution was added to the previously prepared FRTL5 cells, followed by incubation at 37° C. for two hours.

On the other hand, as control, a test was conducted in the same manner using a normal serum.

With respect to each sample, the quantitative analysis of cAMP produced under stimulation by TSAb was conducted by means of a commercially available cAMP-radioimmunoassay kit (1-VQ12, manufactured by Eiken Kagaku Corporation). The results are shown in Table 1.

TABLE 1

| Peptide No. | 30 µg/well | | 15 µg/well | |
| --- | --- | --- | --- | --- |
| | cAMP (nM) | Inhibition rate (%) | cAMP (nM) | Inhibition rate (%) |
| 2 | 1.2 | 85 | 3.4 | 50 |
| 5 | 1.3 | 83 | 3.5 | 48 |
| 7 | 3.1 | 60 | 3.3 | 51 |
| 8 | 1.8 | 76 | 3.2 | 54 |
| Peptide (−) | 7.7 | — | 6.7 | — |
| Control | 1.2 | — | 1.1 | — |

What is claimed is:

1. A peptide having the formula:

A—B—C wherein A is a hydrogen atom, Glu, Phe Glu—, Phe Phe Glu— or the amino acid sequence SEQ ID NO:1 in the Sequence Listing, B is the amino acid sequence SEQ ID NO:2, and C is a hydroxyl group, Glu, —Glu Ile, —Glu Ile Ile or an amino acid sequence selected from the group consisting of SEQ ID NO:3, 4, 5, 6, 7, 8, 9, 10, 11, 12, 13, 14, 15 and 16, and containing from 6 to 25 amino acids; or its salt.

2. The peptide according to claim 1, which has an amino acid sequence selected from the group consisting of:
(1) Phe Glu Glu Gln Glu Asp (SEQ ID NO:18),
(2) Glu Glu Gln Glu Asp Glu (SEQ ID NO:19),
(3) Glu Gln Glu Asp Glu Ile Ile (SEQ ID NO:20),
(4) Phe Phe Glu Glu Gln Glu Asp (SEQ ID NO:21),
(5) Glu Gln Glu Asp Glu Ile Ile (SEQ ID NO:22),
(6) Phe Phe Glu Glu Gln Glu Asp Glu (SEQ ID NO:23),
(7) Phe Glu Glu Gln Glu Asp Glu Ile (SEQ ID NO:24),
(8) Glu Glu Gln Glu Asp Glu Ile Ile (SEQ ID NO:25),
(9) Val Phe Phe Glu Glu Gln Glu Asp (SEQ ID NO:26),
(10) Val Phe Phe Glu Glu Gln Glu Asp Glu (SEQ ID NO:27),
(11) Phe Glu Glu Gln Glu Asp Glu Ile Ile (SEQ ID NO:28),
(12) Glu Glu Gln Glu Asp Glu Ile Ile Gly (SEQ ID NO:29),
(13) Val Phe Phe Glu Glu Gln Glu Asp Glu Ile (SEQ ID NO:30),
(14) Phe Glu Glu Gln Glu Asp Glu Ile Ile Gly (SEQ ID NO:31),
(15) Glu Gln Glu Asp Glu Ile Ile Gly Phe Gly (SEQ ID NO:32),
(16) Phe Glu Glu Gln Glu Asp Glu Ile Ile Gly Phe Gly (SEQ ID NO:33),
(17) Val Phe Phe Glu Glu Gln Glu Asp Glu Ile Ile Gly Phe Gly (SEQ ID NO:34),
(18) Phe Glu Glu Gln Glu Asp Glu Ile Ile Gly Phe Gly Gln Glu Leu (SEQ ID NO:15),
(19) Val Phe Phe Glu Glu Gln Glu Asp Glu Ile Ile Gly Phe Gly Gln Glu Leu (SEQ ID NO:36),
(20) Val Phe Phe Glu Glu Gln Glu Asp Glu Ile Ile Gly Phe Gly Gln Glu Leu Lys Asn Pro (SEQ ID NO:37),
(21) Phe Glu Glu Gln Glu Asp Glu Ile Ile Gly Phe Gly Gln Glu Leu Lys Asn Pro Gln Glu (SEQ ID NO:38),
(22) Phe Glu Glu Gln Glu Asp Glu Ile Ile Gly Phe Gly Gln Glu Leu Lys Asn Pro Gln Glu Glu Thr Leu (SEQ ID NO:39), and
(23) Val Phe Phe Glu Glu Gln Glu Asp Glu Ile Ile Gly Phe Gly Gln Glu Leu Lys Asn Pro Gln Glu Glu Thr Leu (SEQ ID NO:17), or salt thereof.

3. The peptide according to claim 1, which has an amino acid sequence selected from the group consisting of:
(1) Val Phe Phe Glu Glu Gln Glu Asp Glu Ile (SEQ ID NO:30),
(2) Val Phe Phe Glu Glu Gln Glu Asp Glu Ile Ile Gly Phe Gly (SEQ ID NO:34),
(3) Phe Glu Glu Gln Glu Asp Glu Ile Ile Gly Phe Gly Gln Glu Leu (SEQ ID NO:35),
(4) Val Phe Phe Glu Glu Gln Glu Asp Glu Ile Ile Gly Phe Gly Gln Glu Leu Lys Asn Pro (SEQ ID NO:37),
(5) Val Phe Phe Glu Glu Gln Glu Asp Glu Ile Ile Gly Phe Gly Gln Glu Leu Lys Asn Pro Gln Glu Glu Thr Leu (SEQ ID NO:17),
(6) Phe Glu Glu Gln Glu Asp Glu Ile Ile Gly Phe Gly (SEQ ID NO:33),
(7) Val Phe Phe Glu Glu Gln Glu Asp (SEQ ID NO:26), and
(8) Glu Gln Glu Asp Glu Ile Ile Gly Phe Gly (SEQ ID NO:32), or salt thereof.

4. The peptide according to claim 1, which has the amino acid sequence selected from the group consisting of:
(1) Val Phe Phe Glu Glu Gln Glu Asp Glu Ile (SEQ ID NO:30),
(2) Val Phe Phe Glu Glu Gln Glu Asp Glu Ile Ile Gly Phe Gly (SEQ ID NO:34),
(3) Val Phe Phe Glu Glu Gln Glu Asp Glu Ile Ile Gly Phe Gly Gln Glu Leu Lys Asn Pro Gln Glu Glu Thr Leu (SEQ ID NO:17),
(4) Val Phe Phe Glu Glu Gln Glu Asp (SEQ ID NO:26), and
(5) Glu Gln Glu Asp Glu Ile Ile Gly Phe Gly (SEQ ID NO:32), or salt thereof.

5. The peptide according to claim 1, which has an amino acid sequence Val Phe Phe Glu Glu Gln Glu Asp Glu Ile Ile Gly Phe Gly (SEQ ID NO:34) or salt thereof.

* * * * *